United States Patent [19]

Maskalick et al.

[11] Patent Number: 4,617,376
[45] Date of Patent: Oct. 14, 1986

[54] PROCESS FOR RECOVERING GLUCAGON FROM PANCREAS GLANDS

[75] Inventors: David G. Maskalick, Indianapolis; Marie T. Anderson, Greenwood, both of Ind.

[73] Assignee: Eli Lilly and Company, Indianapolis, Ind.

[21] Appl. No.: 833,310

[22] Filed: Feb. 24, 1986

Related U.S. Application Data

[63] Continuation of Ser. No. 750,636, Jul. 1, 1985, abandoned.

[51] Int. Cl.$^4$ ............................................. C07K 7/34
[52] U.S. Cl. ................................. 530/308; 530/415; 530/416
[58] Field of Search .................... 260/112 R, 112.5 R, 260/112.7, 112 B

[56] References Cited

U.S. PATENT DOCUMENTS 3,875,138  4/1975  Jackson ..................... 260/112.5 R
4,033,941  7/1977  Stilz et al. ................. 260/112.5 R
4,221,777  9/1980  Nishino ..................... 260/112 B X

OTHER PUBLICATIONS

D. Bataille, et al., *Hormone Receptors in Digestion and Nutrition*, 79–88 (1979).
D. Fourmy, et al., *J. Liq. Chromatogr.*, 5(11), 2123–1234 (1982).
W. W. Bromer, et al., *J. Biol. Chem.*, 247(8), 2581–2585 (1972).
H. G. Pollock, et al., *J. Biol. Chem.*, 250(24), 9377–9380 (1975).
M. J. O'Hare, et al., *J. Chromatogr.*, 171, 209–226 (1979).

*Primary Examiner*—Howard E. Schain
*Attorney, Agent, or Firm*—William C. Martens, Jr.

[57] ABSTRACT

There is disclosed herein a process for the purification of glucagon from a glucagon salt cake containing pancreas gland-sourced glucagon, which comprises
(1) dissolving said glucagon salt cake in an aqueous medium containing a water-miscible organic solvent;
(2) contacting the glucagon salt cake solution with a hydrophobic adsorption support at a pH less than about 4 or greater than about 7.5 and at conditions under which the glucagon is adsorbed on said hydrophobic adsorption support;
(3) eluting glucagon from said hydrophobic adsorption support with an aqueous solution containing a water-miscible organic solvent to obtain a first glucagon-containing solution;
(4) contacting a solution containing glucagon eluted from said hydrophobic adsorption support, said solution having a pH of from about 7.5 to about 10.5, with an anion exchange support at conditions under which the glucagon is adsorbed on said anion exchange support;
(5) eluting glucagon from said anion exchange support to obtain a second glucagon-containing solution; and
(6) recovering glucagon having increased purity.

21 Claims, No Drawings

PROCESS FOR RECOVERING GLUCAGON FROM PANCREAS GLANDS

This application is a continuation of application Ser. No. 750,636, filed July 1, 1985, now abandoned.

BACKGROUND OF THE INVENTION

Glucagon is a small polypeptide hormone having 29 amino acids. It is synthesized in pancreas islets and exhibits biological action which is the converse of insulin, thereby permitting control of blood glucose level both through glycogenolysis and gluconeogenesis.

The amino acid sequence of porcine glucagon was determined by Bromer, W. W., Sinn, L., and Behrens, O. K., *J. Am. Chem. Soc.* 79, 2801–2805 (1957). Subsequent studies have established that glucagon isolated from other mammalian species is identical to that of porcine glucagon.

Glucagon (molecular weight, 3485 daltons) is synthesized in the A cells of pancreas islets from a precursor molecule estimated to have a molecular weight of about 18,000 to 19,000 daltons. The preprohormone is converted to glucagon through a series of proteolytic cleavages.

Commercial glucagon is available by isolation from bovine or porcine pancreas as a side product during insulin extraction. In extraction of pancreatic insulin, a salt cake can be recovered which contains a predominant quantity of the pancreas-originated glucagon. This salt cake, designated the glucagon salt cake, represents the starting material for the process which is herein defined and which represents the present invention.

SUMMARY OF THE INVENTION

Thus, this invention is directed to a process for the purification of glucagon from a glucagon salt cake containing pancreas gland-sourced glucagon, which comprises
(1) dissolving said glucagon salt cake in an aqueous medium containing a water-miscible organic solvent;
(2) contacting the glucagon salt cake solution with a hydrophobic adsorption support at a pH less than about 4 or greater than about 7.5 and at conditions under which the glucagon is adsorbed on said hydrophobic adsorption support;
(3) eluting glucagon from said hydrophobic adsorption support with an aqueous solution containing a water-miscible organic solvent to obtain a first glucagon-containing solution;
(4) contacting a solution containing glucagon eluted from said hydrophobic adsorption support, said solution having a pH of from about 7.5 to about 10.5, with an anion exchange support at conditions under which the glucagon is adsorbed on said anion exchange support;
(5) eluting glucagon from said anion exchange support to obtain a second glucagon-containing solution; and
(6) recovering glucagon having increased purity.

DETAILED DESCRIPTION OF THE INVENTION

The process of this invention makes available highly pure pancreas-sourced glucagon from glucagon salt cake. The process comprises three discrete and sequential steps, namely, in the order in which they are carried out, (1) hydrophobic absorption chromatography, (2) anion exchange chromatography, and (3) glucagon crystallization.

The hydrophobic adsorption step, of course, involves two stages, application of the glucagon to the hydrophobic adsorption support and elution of glucagon from the support. Although not absolutely essential, a different set of conditions is preferred for each of the hydrophobic adsorption step stages.

The initial glucagon-containing material which is used in the process of this invention is a glucagon salt cake obtained from pancreas extraction or glucagon-containing material of similar make-up. For the purposes herein, the term "glucagon salt cake" is used to broadly encompass any of the foregoing.

The hydrophobic adsorption support typically is a polystyrene copolymer resin, more particularly, a polystyrene-divinylbenzene copolymer resin. Examples of hydrophobic adsorption supports are HP20, HP20-SS, any of the XAD resins, including, for example, XAD-2, XAD-4, XAD-7, and XAD-8. Of particular importance and preference are HP20 and HP20-SS, and most preferably, HP20-SS.

The glucagon salt cake is applied to the hydrophobic adsorption support by dissolving it in an aqueous medium and adjusting the pH of the resulting solution so that it is less than about 4.0 or greater than about 7.5. Although not essential, the solution can be maintained at the selected pH by addition of a salt having buffering capacity at such pH. Examples of such buffers are glycine, Tris, sodium acetate, and the like. A highly preferred buffer, if one is used, is glycine.

As indicated, the pH of the glucagon salt cake solution is maintained above about 7.5 or below about 4.0. The acidic pH is preferred, and, within that range, a pH of from about 2.0 to about 3.6 is most preferred.

Also, although used only for the purpose of solubilizing the glucagon salt cake and therefore not necessarily essential, a water-miscible organic solvent may be added to the glucagon salt cake-aqueous mixture. Examples of useful water-miscible organic solvents are nitriles, for example, acetonitrile, and the like; alcohols, for example, methanol, ethanol, n-propyl alcohol, isopropyl alcohol, and the like; ketones, for example, acetone, and the like; ethers, for example, tetrahydrofuran, dioxane, and the like; and amides, for example, N,N-dimethylformamide, and the like. The water-miscible organic solvent will be added to the aqueous medium in an amount sufficient to effect solubilization of the glucagon salt cake but not so great as to dimminish effective adsorption of the glucagon onto the support. Highly preferred organic solvents are acetonitrile and ethanol, and, of the two, most preferred is acetonitrile. When acetonitrile is used it is added to the aqueous medium in an amount generally not greater than about 20% by volume, sufficient to effect solubilization of the glucagon salt cake without continuous desorption of the adsorbed glucagon. When ethanol is employed, the amount generally can be increased up to about 35% by volume without experiencing continuous glucagon desorption.

Upon adsorption by the hydrophobic support of glucagon from the glucagon salt cake, the support may be washed under conditions which will effect elution of non-glucagon material with retention of the glucagon on the support. The wash medium generally will differ from the application medium by the presence of an increased amount of water-miscible organic solvent. The added amount, although sufficient to cause elution of nonglucagon materials, will be incapable of effecting glucagon elution. Thus, for example, when acetonitrile is used as water-miscible organic solvent, the wash medium may first contain 10% acetonitrile followed by a medium containing 20% acetonitrile. When this sequence is employed, the second wash will effect elution, for example, of pancreatic polypeptide as side product.

Upon completion of the wash step, should one be employed, the glucagon is eluted by step, linear, or a combination of step and linear gradient chromatography. In effecting elution of the glucagon, the eluant composition is altered such that the aqueous, pH-controlled medium contains increasing amounts, whether step-wise or continuous, of water-miscible organic solvent until elution is complete. Thus, if acetonitrile is the selected organic solvent, elution of the glucagon generally will be complete upon the volume composition of the eluant reaching about 35% acetonitrile. If the water-miscible organic solvent is, for example, ethanol, a greater amount of organic solvent may be required, generally up to about 55%.

The glucagon-containing eluate obtained from the foregoing hydrophobic adsorption step of the process of this invention then directly or indirectly is treated as in the second step, i.e., the anion exchange chromatography step.

The anion exchange chromatography support used in the second step of the process of this invention can be selected from any of a wide range of materials. Typically, the support is one containing a functional group such as DEAE (diethylaminoethyl), QAE [diethyl-(2-hydroxypropyl)aminoethyl], and the like. Typical supports containing functional anion exchange groups such as the foregoing are Sephadex (cross-linked dextran bead), Sepharose (agarose bead), Sephacel (cellulose bead), Cellulofine (cellulose bead), Whatman (cellulose), IRA (styrene-divinylbenzene), Monobead (styrene-divinylbenzene), Fractogel (vinyl ether linkage polymer), Trisacryl (acrylic-Tris polymer), and the like. A preferred anion exchange support is DEAE-Sephadex, usually DEAE-Sephadex A25.

The glucagon-containing material obtained directly or indirectly from the hydrophobic adsorption step is applied to the anion exchange chromatography support following adjustment of the pH of the former to the range of from about 7.5 to about 10.5. Preferably, the pH of the glucagon-containing mixture is from about 8.0 to about 9.0, and most preferably, from about 8.0 to about 8.4. Normally, the pH of the mixture will be maintained at the desired level by use of a buffer. Any of a wide range of recognized buffers can be employed. A buffer of choice is tris(hydroxymethyl)aminomethane (Tris).

The glucagon-containing solution applied to Step 2 will contain a solubilizing amount of a water-miscible organic solvent, customarily the same solvent present in the eluant used to elute the glucagon from the hydrophobic adsorption step. Thus, the glucagon solution applied to the anion-exchange column will contain from about 15% to about 50% of a water-miscible organic solvent, typically any of those as described hereinabove for use in solubilizing the glucagon salt cake. Preferred water miscible organic solvents are acetonitrile and ethanol, and most preferably, acetonitrile.

Once applied to the anion exchange column, the glucagon is eluted using an organic-aqueous salt-containing eluant. The typical salt is Tris, and either isocratic or gradient elution can be employed. The latter can be step or linear. The salt concentration will vary depending upon a number of factors, including pH. Thus, the salt concentration must be high enough to displace the glucagon from the anion exchange support and low enough to prevent more tightly bound impurities from eluting along with the glucagon. Generally, the salt concentration will be maintained within the range from about 0.02M to about 1M. The main stream glucagon-containing pool is established by routine methods for detecting proteins.

The third step of the process of this invention involves recovery of glucagon having increased purity. Generally, the recovery is achieved by crystallization and usually directly from the eluate pool obtained from Step 2 of the process of this invention. Glucagon crystals can be obtained merely by cooling the eluate, generally to the range of from about 0° C. to about 5° C. However, in addition to cooling, glucagon crystallization can be facilitated by pH selection and solvent composition. Thus, it is preferred to alter the pH of the glucagon mixture to the range of from about 7.0 to about 8.0, preferably about 7.2, and to reduce the water-miscible organic solvent content, generally to an amount less than about 15% by volume. The concentration of water-miscible organic solvent can be reduced, e.g., by evaporation, dilution, solvent exchange over a size exclusion column, batch adsorption and desorption from a cation exchange resin, and the like. The crystals can be harvested routinely by centrifuging, decanting, or filtering. They then normally are washed with water, dilute NaCl, or ethanol, and lyophilized.

The resulting glucagon, of high purity, is then ready for use.

The following example is provided to illustrate the process of this invention. It is not intended to be limiting upon the scope thereof.

EXAMPLE

A. Step 1-Hydrophobic Adsorption Purification

A 15×100 cm glass column was packed to 90 cm bed height with HP-20SS resin—total resin volume was 16 L. The column was equilibrated in acetonitrile:0.02M glycine (1:9) pH adjusted to 2.8 with HCl. Glucagon salt cake (3.2 kg containing 21.08 g of glucagon) was dissolved in 32 L of acetonitrile:0.02M glycine (1:9) pH 2.8 with stirring for 2 hours at room temperature. The column was charged through a Balston filter at a flow rate of 400 ml/minute—total charge volume was 34 L. The effluent was sampled and then discarded after no glucagon was found to be present. The column was washed with 18 L of acetonitrile:glycine (1:9) pH 2.8 and then with 32 L of acetonitrile:glycine (2:8) pH 2.8 at a flow rate of approximately 400 ml/minute. The first wash was discarded. The second wash was saved since it contained pancreatic polypeptide. No glucagon was in either wash. The column was then eluted with a gradient of a mixing buffer of 32 L of acetonitrile:glycine (20:80) and a limiting buffer of 32 L of acetonitrile:glycine (35:65), both having a pH 2.8. A bulk fraction of 24 L was collected, and then thirty 3 minute fractions (300 ml/minute flow rate) were collected (940 ml each). Every other fraction was analyzed by HPLC, and a mainstream pool of fractions 10-26 and a sidestream pool of fractions 1-9 were made.

The column was regenerated using 70 L of acetonitrile:0.2N sodium hydroxide (50:50), followed by 40 L of acetonitrile:H$_2$O (30:70). The column yield of glucagon was 14.8 g (70.2%) in the main stream pool and 4.1% in the side stream pool (determined by analytical HPLC).

The analytical HPLC system uses a Zorbax C8 150 Å column (4.1×250 mm) with acetonitrile:0.1M phosphate (30:70) pH 2.1. Detection is at 214 nm and the flow rate is 0.7 ml/minute.

B. Step 2—Anion Exchange Purification

A 17.1×40 cm glass column was packed to 28 cm (6.5 L) with DEAE-Sephadex A-25 resin equilibrated in 0.08M Tris-Acetonitrile (70:30), pH adjusted to 8.0 with HCl. The column was sealed with a 50 mm diameter threaded Teflon fitting and a solvent-resistant O-ring, and then was equilibrated with the same buffer overnight at 0.7 L/hr using $N_2$ pressure.

The HP-20SS mainstream pool (14.8 L) was adjusted to pH 8.25 with 10% NaOH (100 ml) and then was applied to the DEAE column at a flow rate of 46 ml/min. The column was stopped after charging, a 1 L buffer head of 0.08M Tris-acetonitrile (70:30) pH 8.0 buffer was applied, and the column then was sealed and elution carried out using a flow rate ranging from 42–50 ml/min. Fractions were collected (22 minutes=1.0–1.1 L each). The eluant was monitored using a uv detector ISCO Model UA-7 at 280 nm—chart speed 1.5 cm/hr—sensitivity 2.0. Fractions were chosen from the uv profile for more accurate measurement of optical density at 276 nm using a spectrophotometer after which a mainstream pool of fractions 13–24 was made (12.6 L). This pool represented a total of 13.23 grams of glucagon or 88.8% of the glucagon applied to the column (14.9 g).

C. Step 3—Glucagon Crystallization

The DEAE mainstream pool was adjusted to pH 10.0 with 430 ml of 1N NaOH and then was concentrated using a rotary evaporator to a volume of 10.96 L which represented a 30% decrease in volume. The concentrated pool was filtered through a CUNO filter (90 SP) in a HEPA-filtered chillroom and then was adjusted to pH 7.20 using 2.32 L of 1N phosphoric acid. The solution was maintained at 4° C. for 3 days during which crystallization occurred. The supernatant was decanted, and the crystal slurry was centrifuged at 5° C., 3000 rpm for 30 minutes. The centrifuged crystals were washed twice with ice cold purified water and then were suspended in purified water, frozen and lyophilized for approximately 36 hours. A total of 9.89 gm of lyophilized powder was obtained containing 9.40 gm glucagon, which represents a 73.1% recovery of glucagon from the DEAE mainstream pool. Total recovery from the glucagon salt cake was 44.6%.

We claim:

1. Process for the purification of glucagon from a glucagon salt cake containing pancreas gland-sourced glucagon, which comprises
   (1) dissolving said glucagon salt cake in an aqueous medium containing a water-miscible organic solvent;
   (2) contacting the glucagon salt cake solution with a hydrophobic adsorption support at a pH less than about 4 or greater than about 7.5 and at conditions under which the glucagon is adsorbed on said hydrophobic adsorption support;
   (3) eluting glucagon from said hydrophobic adsorption support with an aqueous solution containing a water-miscible organic solvent to obtain a first glucagon-containing solution;
   (4) contacting a solution containing glucagon eluted from said hydrophobic adsorption support, said solution having a pH of from about 7.5 to about 10.5, with an anion exchange support at conditions under which the glucagon is adsorbed on said anion exchange support;
   (5) eluting glucagon from said anion exchange support to obtain a second glucagon-containing solution; and
   (6) recovering glucagon having increased purity.

2. Process of claim 1, in which the hydrophobic adsorption support is a polystyrene copolymer resin.

3. Process of claim 2, in which the glucagon salt cake is dissolved in an aqueous medium containing a buffer.

4. Process of claim 3, in which the buffer is glycine.

5. Process of claim 3, in which the pH of the glucagon salt cake solution is maintained below about 4.0.

6. Process of claim 5, in which the pH of the glucagon salt cake solution is from about 2.0 to about 3.6.

7. Process of claim 2, in which the water-miscible organic solvent in the glucagon salt cake-containing aqueous medium is acetonitrile present in an amount not greater than about 20% by volume.

8. Process of claim 2, in which the water-miscible organic solvent in the glucagon salt cake-containing aqueous medium is ethanol present in an amount not greater than about 35% by volume.

9. Process of claim 2, in which, following adsorption of glucagon on the hydrophobic adsorption support, the support is washed under conditions which effect elution of non-glucagon material with retention of glucagon.

10. Process of claim 1, in which the anion exchange support is DEAE-Sephadex.

11. Process of claim 1, in which the glucagon-containing solution contacted with the anion exchange support has a pH of from about 8.0 to about 9.0.

12. Process of claim 11, in which the glucagon-containing solution contacted with the anion exchange support has a pH of from about 8.0 to about 8.4.

13. Process of claim 1, in which the pH of the glucagon-containing solution contacted with the anion exchange support is maintained by addition of tris(hydroxymethyl)aminomethane as buffer.

14. Process of claim 1, in which the glucagon is eluted from the anion exchange support using an organic-aqueous, salt-containing eluant.

15. Process of claim 14, in which the salt is Tris.

16. Process of claim 15, in which the salt concentration is maintained within the range from about 0.02M to about 1M.

17. Process of claim 1, in which glucagon is recovered by crystallization from said second glucagon-containing solution.

18. Process of claim 17, in which glucagon is crystallized from the second glucagon-containing solution by cooling said solution to a temperature in the range of from about 0° C. to about 5° C.

19. Process of claim 18, in which glucagon is crystallized from the second glucagon-containing solution by bringing the pH of said solution to the range of from about 7.0 to about 8.0.

20. Process of claim 19, in which glucagon is crystallized from the second glucagon-containing solution by bringing the pH of said solution to about 7.2.

21. Process of claim 18, in which glucagon is crystallized from the second glucagon-containing solution by reducing the amount of water-miscible organic solvent present in said solution to an amount less than about 15% by volume.

* * * * *